United States Patent [19]

Abplanalp

[11] Patent Number: 4,619,654
[45] Date of Patent: Oct. 28, 1986

[54] OINTMENT APPLICATOR

[76] Inventor: George Abplanalp, 1775 1E Florence Ave., Englewood, Fla. 33533

[21] Appl. No.: 688,815

[22] Filed: Jan. 4, 1985

Related U.S. Application Data

[63] Continuation-in-part of Ser. No. 569,726, Jan. 10, 1984, abandoned.

[51] Int. Cl.$^4$ ............................................. A61M 7/00
[52] U.S. Cl. .................................... 604/897; 604/308
[58] Field of Search ............... 604/308, 307, 304, 305, 604/897, 289; 128/156, 155

[56] References Cited

U.S. PATENT DOCUMENTS

| | | | |
|---|---|---|---|
| 2,858,830 | 11/1958 | Robins | 604/308 X |
| 3,882,867 | 5/1975 | Moran | 604/308 X |
| 4,486,194 | 12/1984 | Ferrara | 604/308 X |

Primary Examiner—Stephen C. Pellegrino
Attorney, Agent, or Firm—Claude A. Patalidis

[57] ABSTRACT

A medication ointment applicator comprising a length of plastic film to which is attached a backing band made of a length of elastic mesh material. The ointment is applied to the surface of the plastic film which is engaged with the skin of the user, the elastic material backing band being wrapped around, for example, the user's ankle or wrist such as to hold the plastic film in firm engagement with the skin for absorption of the medication ointment through the skin. Preferably, the plastic film is provided with a scale enabling the user to measure the correct amount of ointment to be applied as a result of measuring the length of a ribbon of ointment expelled from a dispenser tube, and the surface of the plastic film to which the ointment is applied is textured, in one embodiment of the invention, by ridges being formed on the surface, to help contain the ointment within the edges of the plastic film. In another embodiment of the invention, the plastic film is surrounded by peripheral strips of suitable material that prevents excessive lateral flow of the medicated ointment; such strips being secured to the elastic material as by sewing or by cementation to such material. The backing band of elastic mesh material in one embodiment of the invention has a hook or loop material patch on one end, and lateral strips of complementary hook or loop material at the other end, such that the backing band of elastic mesh material can be wrapped tight and held in position by applying the hook or loop material patch against a portion of the complementary hook or loop material strips. In another embodiment of the invention, a hook-like fastener, applied to one end of the length of elastic material, engages the elastic material when the applicator is applied to a person's body.

6 Claims, 12 Drawing Figures

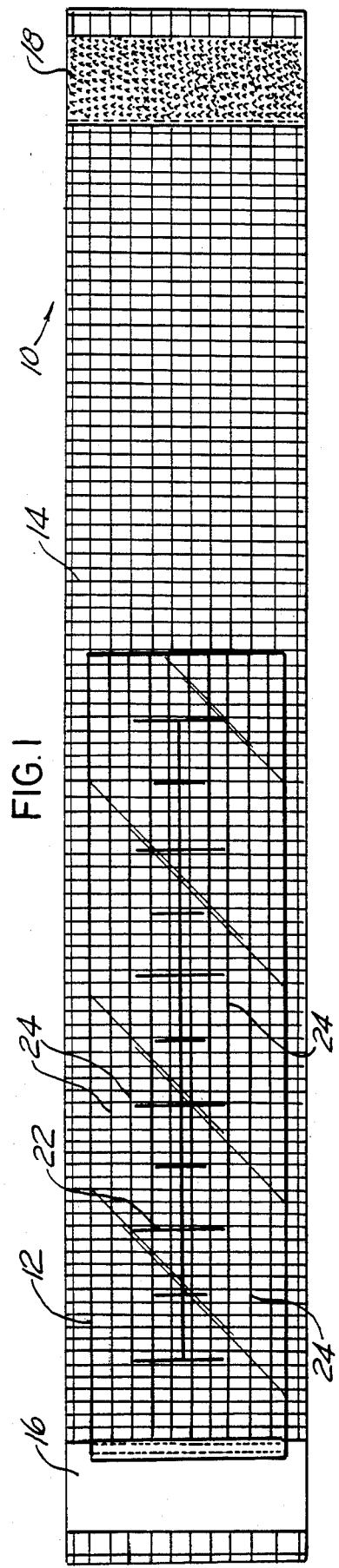
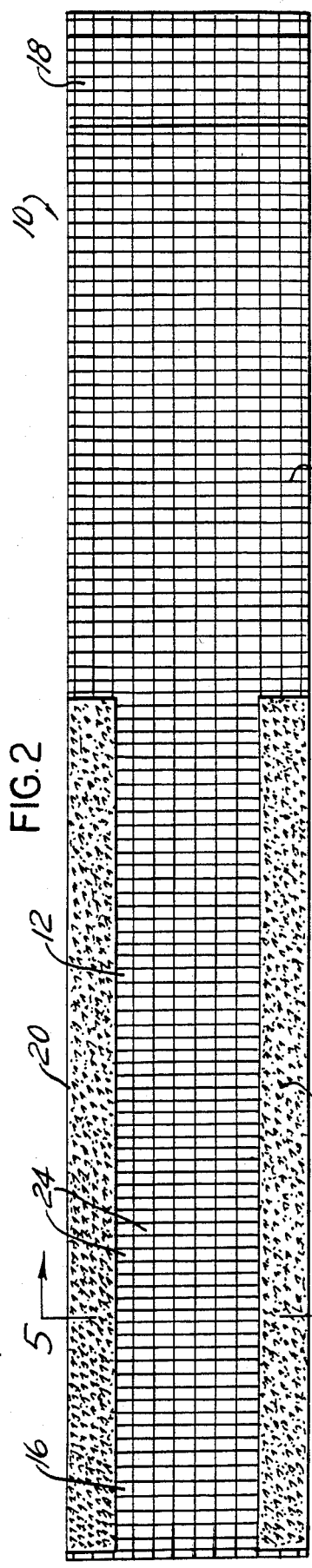
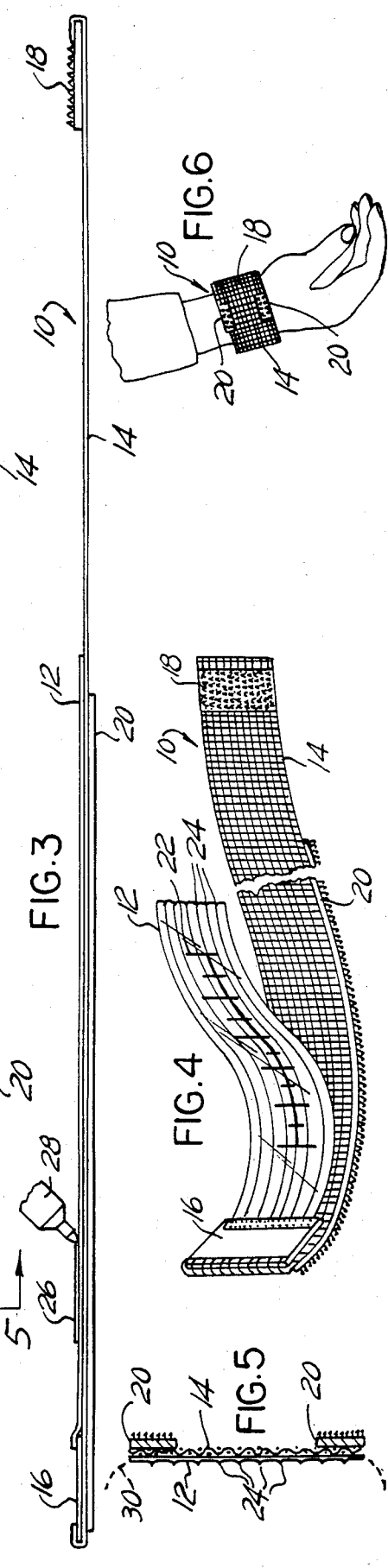

OINTMENT APPLICATOR

CROSS-REFERENCE TO RELATED APPLICATION

The present application is a continuation-in-part of application Ser. No. 569,726, filed Jan. 10, 1984 now abandoned.

BACKGROUND OF THE INVENTION

The present invention relates to a medication ointment applicator.

Medication in the form of an ointment is often dispensed from a container to a bandage which is in turn applied to an area of the body of a patient. The bandage is attached by any convenient means, such as by adhesive tapes, and the medication ointment is slowly absorbed through the skin.

More particularly, nitroglycerine ointment is often dispensed to cardiac patients in the form of an ointment absorbed through the skin. The ointment is dispensed from a tube-like container to a paper applicator. The paper applicator has a printed scale on one surface, and the ointment is squeezed from the neck of the tube-type container in a measured length such as to dispense a prescribed dosage of medication. The paper applicator is translucent such that the printed scale can be seen through the sheet of paper, and the ribbon of ointment dispensed from the tube-type container is applied to the non-printed side of the paper applicator, to prevent contamination of the ointment by the ink used for printing the scale.

The paper applicator is attached by adhesive tape to an area of the body, such as the wrist, the arm, or the ankle, and remains in position until the ointment has been absorbed by the patient through the skin. Since a predetermined dosage of ointment must often be applied several times a day, sometimes as often as every three or four hours, constant application and removal of adhesive tape applicators is somewhat annoying and time consuming, and leads to skin irritations which may become painful.

SUMMARY OF THE INVENTION

The present invention provides a medication ointment applicator bandage permitting to apply a predetermined dosage of medication ointment, such as nitroglycerine, for example, in a safe, easy and painless manner. The ointment applicator bandage of the invention can be repeatedly used, and does not require any adhesive tape for attachment to an area of a patient's body, is neat in appearance as compared to paper applicators, and prevents seepage of the ointment through the applicator or through the edge of the applicator.

This and other advantages of the present invention will become apparent to those skilled in the art when the following description of several modes, contemplated at the present, of the invention is read in conjunction with the accompanying drawing, in which:

BRIEF DESCRIPTION OF THE DRAWING

FIG. 1 is a schematic front elevation view of a medication ointment applicator bandage according to one embodiment of the present invention;

FIG. 2 is a rear elevation view thereof;

FIG. 3 is a side elevation view thereof;

FIG. 4 is a perspective view thereof;

FIG. 5 is a transverse section thereof along line 5—5 of FIG. 2;

FIG. 6 is a view showing the medication ointment applicator bandage of this embodiment of the invention in use;

DETAILED DESCRIPTION OF THE PREFERRED EMBODIMENTS

Figure 7:
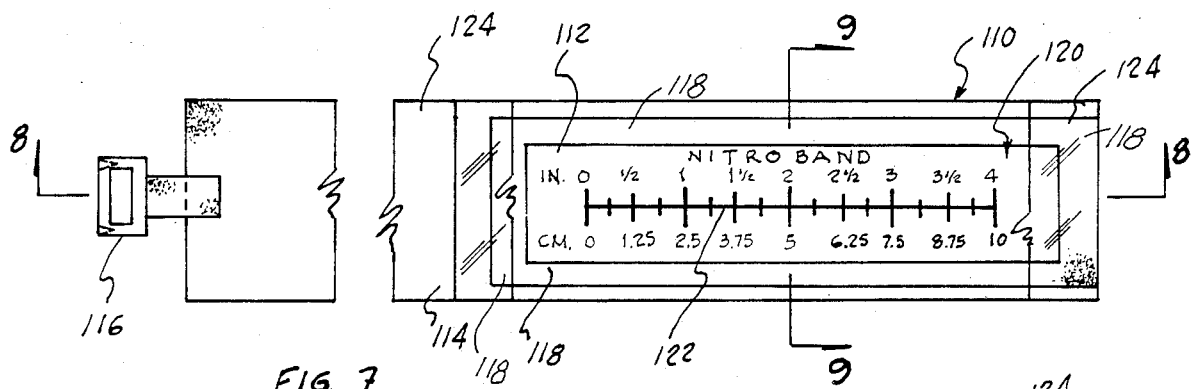
FIG. 7 is a schematic front or plan view of another embodiment of a medication ointment applicator in accordance with the present invention.

Referring to FIGS. 1–6 of the drawing, a medication ointment applicator bandage 10 according to one embodiment of the invention comprises an elongated sheet 12 of transparent or translucent plastic film such as ABS, cellulosic or fluoro plastics, polyamide, polyester, polypropylene, polyvinyl chloride, polyethylene or ethylene copolymers. The sheet 12 of plastic film is attached at one end to a backing band 14 of elastic mesh material either by being sewn or cemented directly onto it, or through the intermediary of a short band 16 of fabric, as shown. The free end of the band 14 of elastic mesh material is provided for example with a patch 18 of plastic hook material, such as sold under the mark Velcro, while the back side of the elastic mesh material is provided with a pair of narrow strips 20 of loop-type material fastener attached, such as by sewing, along each lateral edge of the elastic mesh material band 14.

The sheet 12 of plastic film has its rear surface provided with a printed scale or indicia 22 disposed along the centerline of the sheet, and visible through the transparent or translucent plastic film. The front surface of the sheet 12 of plastic film is textured, for example and as illustrated, by having a plurality of parallel longitudinally extending ridges 24 embossed thereon, such as to project above the front surface, as best shown at FIG. 5.

Figure 8:
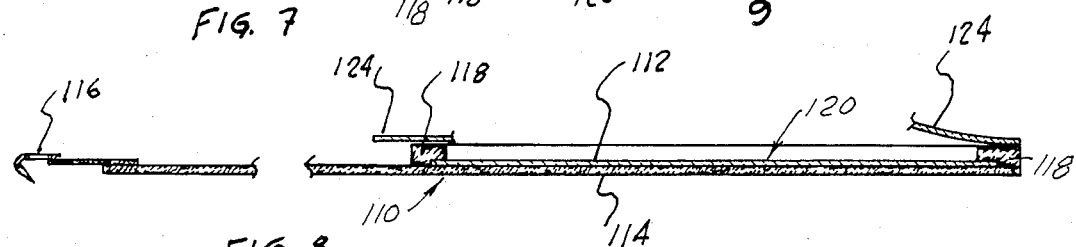
FIG. 8 is a longitudinal sectional view along line 8—8 of FIG. 7.
Figure 9:
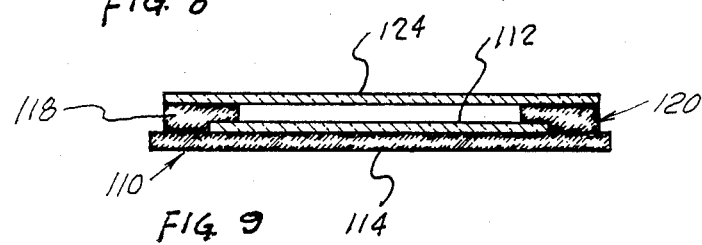
FIG. 9 is a transverse sectional view along line 9—9 of FIG. 7.

Referring now to FIGS. 7–9 of the drawing, a modified medication ointment applicator bandage 110, according to another embodiment of the invention, comprises an elongated sheet 112 of transparent or translucent plastic film that may be the same material as the film 12 of FIG. 1, described hereinbefore. The transparent film or sheet 112 is attached at both ends either by sewing or by being cemented directly to a backing band 114 of elastic mesh material like the band 14 of FIG. 1. One end of the backing band 114 is provided with a conventional hook-like fastener 116 that engages the band 114 to secure the band in a desired position on the body of a person when the band 114 is applied thereto.

Surrounding the plastic film or sheet 112 on all sides are suitable fabric strips 118 that form a margin for a relatively recessed zonal area 120 affording access to the plastic film or sheet 112. The fabric strips 118 may be either sewed or cemented directly to the backing band 114 as preferred.

Applied to the underneath surface of the plastic film or sheet 112 are indicia 122, that are similar to the printed scale 22 shown in FIG. 1 but which are graduated both in inches and centimeters.

Another plastic film or sheet 124, having one end secured to the end of the backing band 114, and having a width equal to the width of the backing band 114, is long enough to cover and extend slightly beyond the left hand edge of the fabric strips 118, as shown in FIG. 8.

Figure 10:
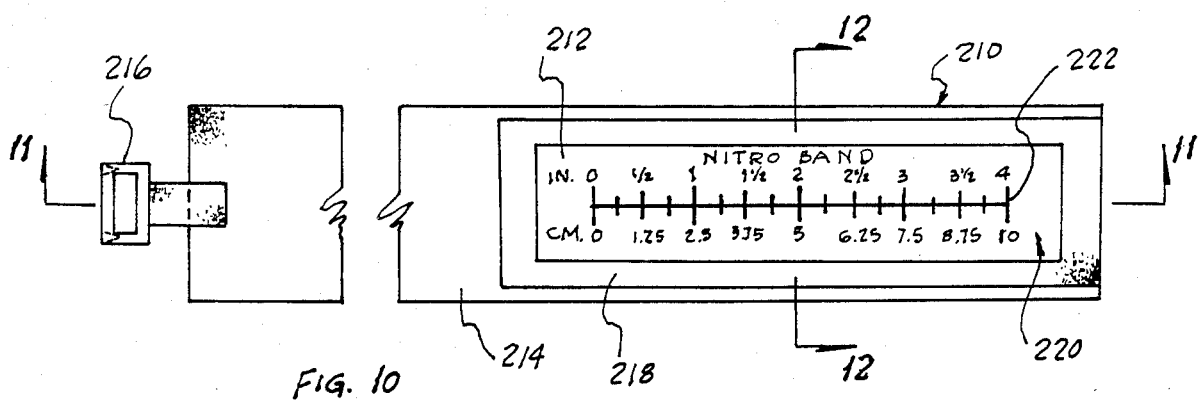
FIG. 10 is a schematic front or plan view of another embodiment of a medication ointment applicator in accordance with the present invention.
Figure 11:
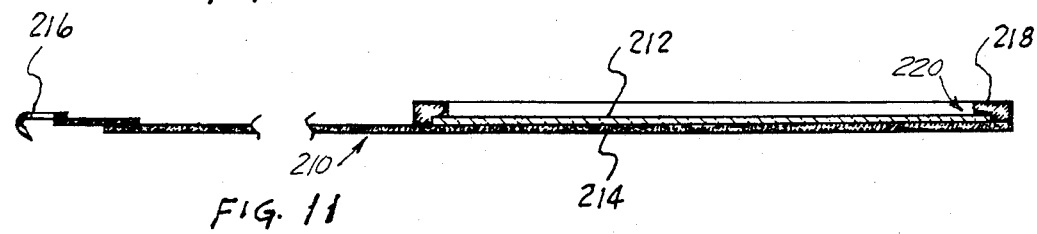
FIG. 11 is a longitudinal sectional view along line 11—11 of FIG. 10.
Figure 12:
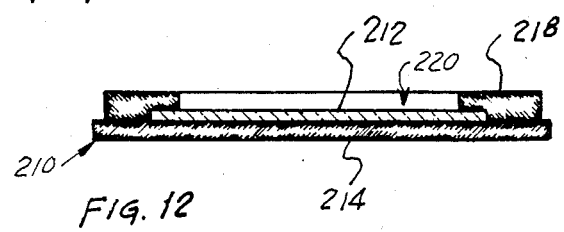
FIG. 12 is a transverse sectional view along line 12—12 of FIG. 10.

Referring to FIGS. 10–12, a medication ointment applicator bandage 210, according to yet another embodiment of the invention, comprises an elongate sheet 212 of transparent or translucent plastic film that may be the same material as the film 12 of FIG. 1, or the film 112 of FIG. 7, described hereinbefore. The transparent film or sheet 212 is attached at both ends by either sewing or cementing it directly to a backing band 214, or in any other suitable manner, preferrably made elastic mesh material like the elastic band 14 of FIG. 1. One end of the elastic mesh backing band 214 is provided with a conventional hook-like fastener 216 that engages the elastic band 214 to secure it in place on the body of a person when the band is applied thereto.

Surrounding the plastic film or sheet 212 on all sides, are suitable fabric or plastic strips 218 that form a relatively recessed open zone 220. These fabric or plastic strips 218 may be secured to the backing band 214 in any suitable manner.

Applied to the underneath surface of the plastic film or sheet 212 are indicia and a printed scale 222 that are similar to the printed scale and indicia 122, shown in FIG. 7. The indicia and scale 222 are graduated both in centimeters and in inches.

In using the ointment applicator bandage 10 of the invention, it is held on a flat surface, as shown at FIG. 3, and a ribbon 26 of ointment such as, for example, nitroglycerine ointment, is applied on the textured surface of the sheet 12 of plastic film, from the neck of a squeeze-tube 28. The dosage of ointment can be determined relatively precisely by applying to the textured surface of the plastic film sheet 12, at its center and along the scale 22, a ribbon 26 of ointment of a predetermined length. The ointment applicator bandage 10 is then wrapped around an area of the body such as, for example, the wrist, FIG. 6, with the textured surface of the plastic film sheet 12 carrying the ribbon 26 of ointment in direct contact with the skin, the elastic mesh band 14 being wound around the wrist, relatively tight, and being held in position by the patch 18 of hook material being applied against a portion of the two strips 20 of complementary loop material. The textured surface of the plastic film sheet 12, provided with the longitudinally extending ridges 24, causes the ointment to be captured in the spaces between consecutive ridges 24 in engagement with a surface 30, FIG. 5, such as the skin of a person, thereby preventing seepage of the ointment in lateral directions beyond the lateral edges of the plastic film sheet 12. If so desired, the textured surface of the plastic film sheet 12 may also be provided with transverse ridges, not shown, such that longitudinal seepage of the ointment beyond the ends of the plastic film sheet 12 or beyond the ridge that determines the dosage, is controlled to a certain degree.

After having maintained the applicator bandage 10 over an appropriate area of a patient's body for a prescribed period of time, re-application of the ointment may be effected simply by pulling the end of the elastic band 14 provided with the pad 18 of hook material such as to separate it from the complementary strips 20 of hook material, unwrapping the applicator bandage 10, reloading the textured surface of the plastic film sheet 12 with a ribbon of ointment of appropriate dosage length, and wrapping and attaching again the applicator bandage 10 in its original or a different position on a person's body.

In using the medication ointment applicator bandage 110, it is first placed on any suitable flat surface and a ribbon 26 of medication ointment, for example nitroglycerine, is applied to the top surface of the plastic film 124, commencing above the zero graduation and extending to the right for a distance equal to the correct dosage. For example, the correct dosage may be a ribbon 2.5 centimeters long which is equal to one inch in length.

The bandage 110 is then applied to the person's body, the ointment being pressed against the person's skin when the bandage is wrapped around an arm, leg or other part of the body, and the portion of the film 124 covered by the ointment is depressed slightly into the zonal area 120, the edges of the film 124 clinging to the person's skin so as to prevent lateral spreading and seepage of the ointment. In using the medication ointment applicator 210, it, too, is placed on a suitable flat surface and a ribbon 26 of medication ointment, for example nitroglycerine, is applied in the zone 220, directly to the top surface of the transparent film or sheet 212, starting from the zero graduation at the left and extending to the right for a distance equal to the correct dosage. For example, the correct dosage may be a ribbon 2.5 centimeters or one inch in length.

The bandage 210 is then applied in the manner previously described to a person's body, and the ointment in the zone 220 than contacts the person's skin, but it is prevented from excessive lateral spreading and seepage because it is confined to the zone 220 by the surrounding strips 218.

Having thus described the present invention by way of typical examples of the structure thereof, other modifications whereof will be apparent to those skilled in the art, but what is claimed as new is as follows:

1. A medication ointment applicator for applying a predetermined amount of medication ointment to a person's skin, said applicator comprising a band of flat plastic pliable film, a band of elastic material of a greater length than said band of plastic film, said band of plastic film being attached to said band of elastic material proximate an end of said band of elastic material, a scale longitudinally disposed substantially along the centerline of the band of plastic film provided with length graduations for measuring a length of ribbon of medication ointment applied to a surface of said plastic film for engagement with a person's skin, strip means disposed surrounding an open area of said plastic film provided with said scale for preventing excessive lateral and longitudinal spreading and seepage of said medication ointment when said applicator is applied to a person's skin, and fastening means at an end of said band of elastic material for attaching said end to a portion of said band of elastic material whereby said applicator is wound around a person's limb with said plastic film carrying said ointment in engagement with the skin of said person.

2. The medication ointment applicator of claim 1 wherein said elastic material is an elastic mesh material.

3. The medication ointment applicator of claim 2 wherein said fastening means comprises a hook fastener at said end of said band of elastic mesh material engageable with said elastic mesh material.

4. A medication ointment applicator for applying a predetermined amount of medication ointment to a person's skin, said applicator comprising a first band of flat plastic pliable film, a band of elastic material of a greater length than said first band of plastic film, said first band of plastic film being attached to said band of elastic material proximate an end of said band of elastic material, a scale longitudinally disposed substantially along the centerline of the first band of plastic film provided with length graduations for measuring a length of ribbon of medication ointment, strip means disposed surrounding an open area of said plastic film provided with said scale, a second band of at least translucent flat plastic pliable film disposed over said first band of plastic film and said strip means such that said scale and length graduations are visible through said second band of plastic film, said second band of plastic film being attached at a single edge to said applicator such that said second band of plastic film is caused to be pliably depressed into a recessed zone surrounded by said strip means for preventing excessive lateral and longitudinal spreading of a ribbon of medication ointment disposed on a surface of said second band of plastic film when said applicator is applied to a person's skin, and fastening means at an end of said band of elastic material for attaching said end to a portion of said band of elastic material whereby said applicator is wound around a person's limb with said plastic film carrying said ointment in engagement with the skin of said person.

5. The medication ointment applicator of claim 4 wherein said elastic material is an elastic mesh material.

6. The medication ointment applicator of claim 5 wherein said fastening means comprises a hook fastener at said end of said band of elastic mesh material engageable with said elastic mesh material.

* * * * *